United States Patent [19]

Childers, Jr. et al.

[11] Patent Number: 4,940,789
[45] Date of Patent: Jul. 10, 1990

[54] 10,11-DIHYDRO-5-ALKYL-12-SUBSTITUTED-10,5-(IMINOMETHANO)-5H-DIBENZO[A,D]CYCLOHEPTENES AS NEUROPROTECTANT AGENTS

[75] Inventors: Wayne E. Childers, Jr., Yardley; Magid A. Abou-Gharbia, Glen Mills, both of Pa.

[73] Assignee: American Home Products Corporation, New York, N.Y.

[21] Appl. No.: 418,591

[22] Filed: Oct. 10, 1989

[51] Int. Cl.$^5$ ............................................ C07D 487/08
[52] U.S. Cl. .................................................. 540/581
[58] Field of Search ........................ 540/581; 514/214

[56]  References Cited
U.S. PATENT DOCUMENTS 3,509,158  4/1970  Dobson et al. ..................... 546/581
3,597,433  8/1971  Dobson et al. ..................... 546/581

FOREIGN PATENT DOCUMENTS 2148  8/1967  South Africa .

OTHER PUBLICATIONS

Brooks et al., J. Chem. Soc., Perkin I, 2588–2591 (1973).
Takayama et al., Chemistry Lett., 865–866 (1978).

Primary Examiner—Cecilia Shen
Attorney, Agent, or Firm—Richard K. Jackson

[57] ABSTRACT

This invention involves novel neuroprotectant agents of the formula:

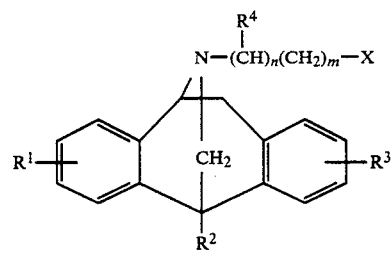

in which $R^1$ and $R^3$ are, independently, hydrogen, alkyl, alkoxy, hydroxy, cyano, nitro, halo, trifluoromethyl, amino, alkylamino or dialkylamino; $R^2$ is alkyl; $R^4$ is alkyl, phenyl or benzyl; n is 0 or 1; m is one of the integers 0,1,2,3,4,5 or 6; and X is alkyl, alkylamino, dialkylamino, alkanoyl or substituted or unsubstituted phenyl, pyridinyl, pyrimidinyl, pyrazinyl, quinolyl, morpholinyl, furyl thienyl, pyrrolyl, tetrahydrofuryl, tetrahydrothienyl, pyrrolidinyl, piperidinyl, piperazinyl or perhydropyridminyl, in which the subsitutent is alkyl, alkoxy, halo, trifluoromethyl, cyano, nitro or hydroxy; or a pharmaceutically acceptable salt thereof; and their use in control of degenerative CNS disease states.

13 Claims, No Drawings

10,11-DIHYDRO-5-ALKYL-12-SUBSTITUTED-10,5-(IMINOMETHANO)-5H-DIBENZO[A,D]CY-CLOHEPTENES AS NEUROPROTECTANT AGENTS

BACKGROUND OF THE INVENTION

Antagonism of the centrally-acting excitatory amino acids (EAA), especially at the N-methyl-D-aspartate (NMDA)-specific receptor complex, is believed to represent a useful approach to the treatment of several CNS disorders, including senile dementia, Alzheimer's disease, Huntingdon's chorea, stroke, hypoglycemia, cerebral palsy, cerebral ischemia, epilepsy, and olivo-ponto-cerebellar atrophy. Two approaches to NMDA-antagonism have been pursued in recent years, namely competitive antagonism of the NMDA receptor and noncompetitive blockade of the NMDA-associated ion channel. To date, noncompetitive antagonists have proved more potent and more orally active than their competitive counterparts in blocking NMDA-induced responses in vivo and in protecting against cell death associated with induced cerebral ischemia.

Data suggest that phencyclidine (PCP) and other related "dissociative anesthetics" noncompetitively antagonize NMDA-induced responses by binding to the NMDA-associated ion channel and blocking ion permeability. Unfortunately, PCP possesses undesirable psychotomimetic side effects and causes ataxia in several animal models. In fact, the separation between a compounds's NMDA-antagonist activity and ataxic activity (often expressed as an "efficacy ratio" of the $ED_{50}$'s of these two activities) has been extensively used to evaluate its therapeutic usefulness versus its liabilities. In our studies, PCP is approximately equipotent in its abilities to antagonize NMDA-induced lethality in mice and cause ataxia as measured by the traction reflex deficit model, giving an efficacy ratio ($ED_{50}/TD_{50}$) of approximately 1.4 (Table 1, infra).

The most potent noncompetitive NMDA-antagonist reported to date is MK-801. Like PCP, MK-801 antagonizes NMDA-induced lethality and protects against cell death in cerebral ischemia models. However, MK-801 competes for the high-affinity PCP binding site in the NMDA-associated ion channel. Furthermore, like PCP, there is no separation between MK-801's ability to antagonize NMDA-induced lethality and cause ataxia (efficacy ratio=0.9, Table 1 infra). In fact, the drug discrimination experiments, MK-801 generalizes for PCP, suggesting that MK-801 may possess PCP-like psychotomimetic side effects.

Dextromethorphan, an over-the-counter antitussive, also noncompetitively antagonizes NMDA-induced responses (Table 1, infra). Its proposed binding site in the ion channel may be different from that shared by PCP and MK-801. While not as potent as PCP and MK-801 in antagonizing NMDA-induced lethality, dextromethorphan shows a better antagonism/ataxia efficacy ratio (2.1). However, dextromethorphan is metabolized to dextrorphan in man. Dextrorphan's efficacy ratio is essentially the same as that for dextromethorphan, but data suggests that dextrorphan may exert its effects by interacting with the high-affinity PCP binding site in the NMDA-associated ion channel. This fact again raises the question of PCP-like psychotomimetic side effects.

DESCRIPTION OF THE INVENTION

In accordance with this invention, there is provided a group of novel compounds which because of their CNS activity profile are considered to be useful in the treatment of neurodegenerative diseases such as Alzheimer's disease, Huntingdon's chorea, senile dementia, Parkinson's syndrome, and olivo-ponto-cerebellar atrophy, as well as epilepsy, stroke, hypoglycemia and cerebral ischemia.

Compounds of the present invention are described by the generic formula:

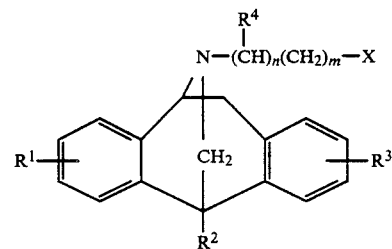

in which
R$^1$ and R$^3$ are, independently, hydrogen, alkyl of 1 to 6 carbon atoms, alkoxy of 1 to 6 carbon atoms, hydroxy, cyano, nitro, halo, trifluoromethyl, amino, alkylamino of 1 to 6 carbon atoms or dialkylamino of 2 to 12 carbon atoms;
R$_2$ is alkyl of 1 to 6 carbon atoms;
R$^4$ is alkyl of 1 to 6 carbon atoms, phenyl or benzyl;
n is 0 or 1;
m is one of the integers 0, 1, 2, 3, 4, 5 or 6; and
X is alkyl of 1 to 6 carbon atoms, alkylamino of 1 to 6 carbon atoms, dialkylamino in which each alkyl group has 1 to 6 carbon atoms, alkanoyl of 2 to 6 carbon atoms or substituted or unsubstituted phenyl, pyridinyl, pyrimidinyl, pyrazinyl, quinolyl, morpholinyl, furyl, thienyl, pyrrolyl, tetrahydrofuryl, tetrahydrothienyl, pyrrolidinyl, piperidinyl, piperazinyl or perhydropyrimidinyl, in which the substituent is alkyl of 1 to 6 carbon atoms, alkoxy of 1 to 6 carbon atoms, halo, trifluoromethyl, cyano, nitro or hydroxy;
or a pharmaceutically acceptable salt thereof.

Preferred neuroprotectants from the standpoint of production economics and activity profile are those of the formula:

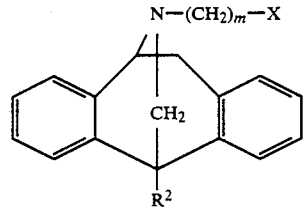

in which
R$^2$ is alkyl of 1 to 3 carbon atoms;
m is one of the integers 0, 1, 2, 3 or 4; and
X is alkyl of 1 to 4 carbon atoms, alkylamino of 1 to 4 carbon atoms, dialkylamino of 2 to 8 carbon atoms, alkanoyl of 2 to 4 carbon atoms, phenyl, pyridinyl, 2-pyrimidinyl, 2-pyrazinyl, 2-quinolinyl, 2-furyl, 2-thienyl or 2-pyrrolyl;

or a pharmaceutically acceptable salt thereof.

The pharmaceutically acceptable salts of the compounds of this invention are prepared conventionally from organic or inorganic acids such as acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention may be prepared via a variety of routes using conventional methods and commercially available starting materials. Thus, the desired substituted and unsubstituted 10,11-dihydro-5-alkyl-10,5-(iminomethano)-5H-dibenzo[a,d]cycloheptenes can be prepared from appropriately substituted 1,2-diphenylethylamines using the methods of R. D. Waigh, et al., J. Chem. Soc., Perkin I (1973), 2588, and H. Takayama, et al., Chem. Lett. (1978), 865, employing a suitably substituted propargyl halide. These unsubstituted amines can, in turn, be converted to N-alkylated, N-aralkylated and N-dialkylaminoalkylated analogs either by treatment with an appropriately substituted alkyl halide in the presence of a suitable base such as triethylamine, or via the Leukhart-Wallach Reaction employing an appropriate carbonyl compound and a suitable acid such as formic acid. Alternatively, the unsubstituted amines can be converted to desired amides by treatment with an appropriate acid halide in the presence of a suitable base such as triethylamine.

The desired alkylheterocyclic analogs can be obtained from the unsubstituted amines either by treatment with an appropriately substituted alkyl halide in the presence of a suitable base such as triethylamine, or by treatment of the unsubstituted amine with an appropriate vinylheteroaromatic reagent in the presence of a suitable acid such as acetic acid.

The following examples illustrate, without limitation, the preparation of representative compounds of this invention.

EXAMPLE 1

10,11-Dihydro-5,12-dimethyl-10,5-(iminomethano)-5H-dibenzo[a,d]cycloheptene

To a stirred mixture of 10,11-dihydro-5-methyl-10,5-(iminomethano)-5H-dibenzo[a,d]cycloheptene (0.5 g, $2.13 \times 10^{-3}$ mol) and 37% aqueous formaldehyde (3.0 ml, $4.0 \times 10^{-2}$ mol) was added 96% formic acid (3.0 ml, $8.0 \times 10^{-2}$ mol). The resulting solution was stirred at 100° C. for 2 hours. The cooled solution was then concentrated on a rotary evaporator. The resulting yellow solid was triturated with three 10 ml portions of diethyl ether to remove formaldehyde polymers. The residue was then dissolved in 50 ml of 2.5N aqueous NaOH, and the basic mixture was extracted with three 25 ml portions of dichloromethane. The combined organic layers were dried over anhydrous sodium sulfate and concentrated on a rotary evaporator to give the title compound as an oil which did not require further purification (TLC on silica gel using a 1:1 dichloromethane/methanol solvent system, $R_f = 0.68$). The amine was converted to the hydrochloride salt with isopropanolic HCl (0.48 g, 91% yield), mp=248°-249° C.

Elemental analysis for $C_{18}H_{19}N \cdot HCl \cdot 1/16H_2O$. Calc'd: C, 75.34; H, 7.07; N, 4.88. Found: C, 74.95; H, 7.09; N, 4.66.

EXAMPLE 2

10,11-Dihydro-5-methyl-12-[2-(2-pyridinyl)ethyl]10,5-(iminomethano)-5H-dibenzo[a,d]cycloheptene A stirred solution of 10,11-dihydro-5-methyl-10,5-(iminomethano)-5H-dibenzo[a,d]cycloheptene (0.5 g, $2.13 \times 10^{-3}$ mol), 2-vinylpyridine (0.26 g, $2.5 \times 10^{-3}$ mol), and glacial acetic acid (0.35 ml) in 15 ml of methanol was allowed to reflux under a dry nitrogen atmosphere for 48 hours. Reflux was then halted and the cooled mixture was concentrated on a rotary evaporator. The residue was treated with 50 ml of saturated aqueous sodium bicarbonate and the pH was adjusted to 8.5 by addition of a solid sodium bicarbonate. The aqueous mixture was then extracted with three 100 ml portions of chloroform. The combined organic extracts were dried over anhydrous sodium sulfate and concentrated on a rotary evaporator. The desired product (TLC on silica gel using a 1:1 dichloromethane/methanol solvent system, $R_f = 0.7$) was isolated by preparative HPLC on silica gel using a gradient of 20% ethyl acetate in dichloromethane to 20% methanol in ethyl acetate to give the title compound which was converted to the dihydrochloride salt (0.31 g, 35% yield), mp=193°-195° C.

Elemental analysis for $C_{24}H_{24}N_2 \cdot 2HCl$. Calc'd: C, 69.73; H, 6.34; N, 6.78. Found: C, 69.62; H, 6.22; N, 6.68.

EXAMPLE 3

10,11-Dihydro-5-methyl-12-[2-(4-pyridinyl)ethyl]10,5-(iminomethano)-5H-dibenzo[a,d]cycloheptene A stirred solution of 10,11-dihydro-5-methyl-10,5-(iminomethano)-5H-dibenzo[a,d]cycloheptene (0.5 g, $2.13 \times 10^{-3}$ mol), 4-vinylpyridine (0.26 g, $2.5 \times 10^{-3}$ mol), and glacial acetic acid (0.36 ml) in 15 ml of methanol was allowed to reflux under a dry nitrogen atmosphere for 72 hours. Reflux was then halted and the cooled mixture was concentrated on a rotary evaporator. The residue was treated with 50 ml of saturated aqueous sodium bicarbonate and the pH was adjusted to 8.5 by addition of a solid sodium bicarbonate. The aqueous mixture was then extracted with three 100 ml portions of chloroform. The combined organic extracts were dried over anhydrous sodium sulfate and concentrated on a rotary evaporator. The title compound (TLC on silica gel using a 5% methanol/dichloromethane solvent system, $R_f = 0.57$) was isolated by preparative HPLC on silica gel using a gradient of 20% methanol in dichloromethane to 100% methanol and converted to the dihydrochloride salt with isopropanolic HCl (0.28 g, 33% yield), mp=335°-337° C.

Elemental analysis for $C_{24}H_{24}N_2 \cdot 2HCl \cdot \frac{3}{4}H_2O$. Calc'd: C, 67.52; H, 6.49; N, 6.56. Found: C, 67.52; H, 6.80; N, 6.27.

EXAMPLE 4

10,11-Dihydro-5-methyl-12-(2-pyrazinylethyl)-10,5-(iminomethano)-5H-dibenzo-cycloheptene A stirred mixture of 10,11-dihydro-5-methyl-10,5-(iminomethano)-5H-dibenzo[a,d]cycloheptene (0.75 g, $3.2 \times 10^3$ mol), 2-vinylpyrazine (34 g of 10% w/w solution in propylene glycol containing 3.4 g ($3.2 \times 10^{-2}$ mol) of 2-vinylpyrazine), and glacial acetic acid (0.5 ml) was heated at 120° C. under a dry nitrogen atmosphere for 72 hours. Heating was then halted and the cooled mixture was concentrated under high vacuum on a rotary evaporator. The residue was treated with 100 ml of 5% aqueous sodium bicarbonate and the pH of the mixture was adjusted to 8.5 by addition of solid sodium bicarbonate. The aqueous mixture was then extracted with three 150 ml portions of chloroform. The combined organic extracts were dried over anhydrous sodium sulfate and concentrated on a rotary evaporator. The dark brown residue was partially purified by passing it across a silica gel column (200 g silica gel) using 1:1 methanol/dichloromethane as the eluent. The title compound (TLC on silica gel using a 5% methanol/dichloromethane solvent system, $R_f=0.6$) was isolated from the resulting residue by preparative HPLC using a gradient of 1:1 ethyl acetate/hexane to 20% methanol/ethyl acetate and converted to the dihydrochloride salt with isopropanolic HCl (0.31 g, 25% yield), mp=134°–135° C.

Elemental analysis for $C_{23}H_{23}N_3 \cdot 2HCl$. Calc'd: C, 66.67; H, 6.08; N, 10.14. Found: C, 66.46; H, 6.14; N, 10.33.

EXAMPLE 5

10,11-Dihydro-N,N,5-trimethyl-10,5-(iminomethano)-5H-dibenzo[a,d]cycloheptene-12-propanamine A stirred mixture of 10,11-dihydro-5-methyl-10,5-(iminomethano)-5H-dibenzo[a,d]cycloheptene (0.5 g, $2.13 \times 10^{-3}$ mol), 3-chloro-N, N-dimethylaminopropane hydrochloride (0.51 g, $3.2 \times 10^{-3}$ mol), and triethylamine (0.88 g, $8.5 \times 10^{-3}$ mol) in 20 ml of dry dimethylformamide was heated at 75° C. under a dry nitrogen atmosphere for 18 hours. The mixture was then concentrated on a rotary evaporator under high vacuum and the residue was partitioned between 100 ml of dichloromethane and 100 ml of 5% aqueous sodium bicarbonate. The aqueous layer was extracted with an additional 50 ml portion of dichloromethane and the combined organic layers were dried over anhydrous sodium sulfate and concentrated on a rotary evaporator. The desired product (TLC on silica gel using 1:1 methanol/dichloromethane with 1% concentration aqueous ammonia, $R_f=0.50$) was isolated by chromatography on silica gel using 1:1 methanol/dichloromethane with 1% concentration aqueous ammonia and converted to the dihydrochloride salt with isopropanolic HCl (0.33 g, 43% yield), mp=251°–252° C.

Elemental analysis for $C_{22}H_{28}N_2 \cdot 2HCl$. Calc'd: C, 67.16; H, 7.64; N, 7.12. Found: C, 66.36; H, 7.79; N, 6.77.

EXAMPLE 6

10,11-Dihydro-5-methyl-12-(2-pyridinylmethyl)-10,5-(iminomethano)-5H-dibenzo[a,d]cycloheptene A stirred mixture of 10,11-dihydro-5-methyl-10,5-(iminomethano)-5H-dibenzo[a,d]cycloheptene (0.75 g, $3.2 \times 10^{-3}$ mol), 2-picolyl chloride hydrochloride (0.52 g, $3.2 \times 10^{-3}$ mol), and diisopropylethylamine (1.62 g, $1.62 \times 10^{-2}$ mol) in 35 ml of dry dimethylformamide was heated at 80° C. under a dry nitrogen atmosphere for 18 hours. The mixture was then concentrated on a rotary evaporator under high vacuum and the residue was partitioned between 150 ml of dichloromethane and 100 ml of 5% aqueous solution bicarbonate. The aqueous layer was extracted with an additional 50 ml portion of dichloromethane and the combined organic layers were dried over anhydrous sodium sulfate and concentrated on a rotary evaporator. The desired product (TLC on silica gel using 3% methanol/dichloromethane, $R_f=0.41$) was isolated by chromatography on silica gel using 3% methanol/dichloromethane and converted to the dihydrochloride salt with isopropanolic HCl (0.37 g, 30% yield), mp=214°–217° C.

Elemental analysis for $C_{23}H_{22}N_2 \cdot 2HCl$. Calc'd: C, 69.17; H, 6.06; N, 7.01. Found: C, 68.13; H, 6.18; N, 6.40.

EXAMPLE 7

10,11-Dihydro-5-methyl-12-[2-(2-quinolinyl)ethyl]-10,5-(iminomethano)-5H-dibenzo[a,d]cycloheptene A stirred mixture of 10,11-dihydro-5-methyl-10,5-(iminomethano)-5H-dibenzo[a,d]cycloheptene (0.75 g, $3.2 \times 10^{-3}$ mol), 2-vinylquinoline (0.68 g, $4.4 \times 10^{-3}$ mol) and glacial acetic acid (0.25 ml) in 30 ml of absolute methanol was refluxed at 80° C. under a dry nitrogen atmosphere for 48 hours. The mixture was then concentrated on a rotary evaporator and the residue was partitioned between 150 ml of dichloromethane and 150 ml of 5% aqueous sodium bicarbonate. The organic layer was dried over anhydrous sodium sulfate and concentrated on a rotary evaporator. The desired product (TLC on silica gel using 5% methanol/dichloromethane, $R_f=0.32$) was isolated by chromatography on silica gel using 5% methanol/dichloromethane and converted to the dihydrochloride salt with isopropanolic HCL (0.66 g, 45% yield), mp=210°–212° C.

Elemental analysis for $C_{28}H_{26}N_2 \cdot 2HCl \cdot 0.5H_2O$. Calc'd: C, 69.84; H, 6.07; N, 5.81. Found: C, 70.21; H, 6.28; N, 5.63.

EXAMPLE 8

10,11-Dihydro-5-methyl-12-[2-(6-methyl-2-pyridinyl)ethyl]-10,5-(iminomethano)-5H-dibenzo[a,d]cycloheptene A stirred mixture of 10,11-dihydro-5-methyl-10,5-(iminomethano)-5H-dibenzo[a,d]cycloheptene (0.75 g, $3.2 \times 10^{-3}$ mol), 6-methyl-2-vinylpyridine (0.57 g, $4.8 \times 10^{-3}$ mol), prepared according to the procedure of Prasad and Raper, J. Chem. Soc. (1956) 217–19, and glacial acetic acid (0.27 ml) in 30 ml of absolute methanol was refluxed at 85° C. under a dry nitrogen atmosphere for 36 hours. The mixture was then concentrated on a rotary evaporator and the residue was partitioned between 150 ml of dichloromethane and 150 ml of 5% aqueous sodium bicarbonate. The organic layer was dried over anhydrous sodium sulfate and concentrated on a rotary evaporator. The desired product (TLC on silica gel using 3% methanol/dichloromethane, $R_f=0.37$) was isolated by chromatography on silica gel using 3% methanol/dichloromethane and converted to the dihydrochloride salt with isopropanolic HCl (0.57 g, 40% yield), mp=173°–175° C.

Elemental analysis for $C_{25}H_{26}N_2 \cdot 2HCl \cdot 1.5H_2O$. Calc'd: C, 66.07; H, 6.87; N, 6.15. Found: C, 66.03; H, 6.99, N. 5.51.

EXAMPLE 9

10,11-Dihydro-5-methyl-12-(2-phenylethyl)-10,5-(iminomethano)-5H-dibenzo[a,d]cycloheptene A stirred mixture of 10,11-dihydro-5-methyl-10,5-(iminomethano)-5H-dibenzo[a,d]cycloheptene (0.85 g, $3.6 \times 10^{-3}$ mol), 2-chloroethylbenzene (0.51 g, $3.6 \times 10^{-3}$ mol), and triethylamine (1.83 g, $1.83 \times 10^{-2}$ mol) in 35 ml of dry dimethylformamide was heated at 80° C. under a dry nitrogen atmosphere for 18 hours. Another portion of 2-chloroethylbenzene (0.51 g, $3.6 \times 10^{-3}$ mol), was then added and heating was continued for an additional 24 hours. The mixture was then concentrated on a rotary evaporator under high vacuum and the residue was partitioned between 150 ml of dichloromethane and 100 ml of 5% aqueous sodium bicarbonate. The aqueous layer was extracted with an additional 50 ml portion of dichloromethane and the combined organic layers were dried over anhydrous sodium sulfate and concentrated on a rotary evaporator. The desired product (TLC on silica gel using 1% methanol/dichloromethane, $R_f=0.51$) was isolated by chromatography on silica gel using 1% methanol/dichloromethane and converted to the hydrochloride salt with isopropanolic HCl (0.21 g, 16% yield), mp=228°–230° C.

Elemental analysis for $C_{25}H_{25}N \cdot HCl \cdot 0.5H_2O$. Calc'd: C, 77.99; H, 7.07; N, 3.64. Found: C, 77.83; H, 6.83; N, 3.73.

EXAMPLE 10

10,11-Dihydro-5-methyl-12-(2-propyl)-10,5-(iminomethano)-5H-dibenzo[a,d]cycloheptene A stirred mixture of 10,11-dihydro-5-methyl-10,5-(iminomethano)-5H-dibenzo[a,d]cycloheptene (0.98 g, $4.2 \times 10^{-3}$ mol), 2-bromopropane (1.17 ml, $1.25 \times 10^{-2}$ mol), and anhydrous potassium carbonate (2.91 g, $2.1 \times 10^{-2}$ mol) in 35 ml of dry dimethylformamide was heated at 50° C. under a dry nitrogen atmosphere for 24 hours. Another portion of 2-bromobenzene (1.17 ml, $1.25 \times 10^{-2}$ mol) was then added and heating was continued for an additional 48 hours. The mixture was then concentrated on a rotary evaporator under high vacuum and the residue was partitioned between 200 ml of dichloromethane and 100 ml of 5% aqueous sodium bicarbonate. The aqueous layer was extracted with an additional 50 ml portion of dichloromethane and the combined organic layers were dried over anhydrous sodium sulfate and concentrated on a rotary evaporator. The desired product (TLC on silica gel using 5% methanol/dichloromethane, $R_f=0.41$) was isolated by chromatography on silica gel using 5% methanol/dichloromethane and converted to the hydrochloride salt with isopropanolic HCl (0.48 g, 37% yield), mp=218°–219° C.

Elemental analysis for $C_{20}H_{23}N \cdot HCl$. Calc'd: C, 76.53; H, 7.71; N, 4.46. Found: C, 76.67; H, 7.61; N, 4.55.

EXAMPLE 11

10,11-Dihydro-5-methyl-10,5-(iminomethano)-5H-dibenzo[a,d]cycloheptene-12-acetamide A stirred mixture of 10,11-dihydro-5-methyl-10,5-(iminomethano)-5H-dibenzo[a,d]cycloheptene (0.5 g, $2.13 \times 10^{-3}$ mol), triethylamine (0.3 g, $3.0 \times 10^{-3}$ mol), and acetic anhydride (0.3 g, $3.0 \times 10^{-3}$ mol) in anhydrous diethyl ether were stirred at room temperature under a dry nitrogen atmosphere for 1 hour. The mixture was then washed with water, 2N aqueous anhydrous HCl, saturated aqueous sodium bicarbonate, and water, and the organic layer was dried over anhydrous magnesium sulfate and concentrated on a rotary evaporator. The desired product (TLC on silica gel using ethyl acetate, $R_f$=0.80) was isolated by crystallization from cold methanol (0.45 g, 76% yield), mp=174°–175° C.

Elemental analysis for $C_{19}H_{19}NO$. Calc'd: C, 82.28; H, 6.90; N, 5.05. Found: C, 82.28; H, 7.20; N, 4.81.

The properties of these compounds were directly established by demonstrating the NMDA antagonist properties of representative compounds in male Swiss-albino mice (CD-1 strain, Charles River) 18–22 grams in weight after 18 hours of food deprivation which had been habituated to an observation chamber for 30 minutes. The mice were pretreated with the representative test compounds followed thirty minutes later with NMDA (195 mg/kg, i.p., the $ED_{90}$ dose for generalized myoclonus). The mice were then observed for 30 minutes, noting the latency of onset of generalized myoclonus (uncontrollable hind leg scratching or limbs and/or torso muscle jerking with loss of righting reflex) and death. From the latter, the $ED_{50}$ for survival is determined. In this standard experimental test procedure, the specific compounds tested and their activity, which representatively establish the activity for all the compounds herein, is presented in Table I as follows:

TABLE 1

| | NMDA-Induced Lethality and Traction Reflex Deficit (Ataxia) | | | | |
|---|---|---|---|---|---|
| Compound of Example | *$ED_{50}$ Inhibition of NMDA-Induced Lethality (mg/kg) | | | @$TD_{50}$-Traction Reflex Deficit, I.P. (mg/kg) | Efficacy Ratio ($ED_{50}/TD_{50}$) |
| | +I.P. | ≠P.O. | IP/PO Ratio | | |
| 1 | 3.1 | | | 13 | 4.2 |
| 2 | 9.8 | | 0.57 | 67 | 6.8 |
| 3 | 18 | | | 83 | 4.6 |
| 4 | 12 | | | 30 | 2.5 |
| 5 | #66% at 100 mg/g | | | | |
| 6 | #66% at 20 mg/kg | | | | |
| 7 | >20 mg/kg | | | | |
| 8 | 13 | | | 68 | 5.1 |
| 9 | #17% at 20 mg/kg | | | | |
| 10 | #100% at 10 mg/kg | | | | |
| 11 | #10% at 10 mg/kg | | | | |
| PCP | 1.9 | | | 2.7 | 1.4 |
| MK-801 | 0.19 | 0.32 | 0.58 | 0.17 | 0.9 |
| Dextromethorphan | 21 | | | 45 | 2.1 |
| Dextrorphan | 13 | | | 29 | 2.2 |

*As measured in mice. Defined as the dose required to produce 50% survival rate.
@As measured in mice. Defined as the dose which produced the deficit in 50% of animals tested.
+Intraperitoneal injection.
≠Oral administration.
Percent of animals which survived at the dose indicated.

In addition, the compounds involved herein were established as inhibitors of NMDA-induced neuronal release of norepinephrine by showing that NMDA-induced norephinephrine release at 100 μM concentration of inhibitor was reduced in the following standard test procedure:

Rat hippocampal slices (0.5 mm thick) were incubated (37° C.) for 30 minutes in oxygenated (bubbled 95% O₂/5% CO₂), physiological medium (containing 117 mM NaCl, 4.7 mM KCl, 11.5 mM glucose, 1.2 mM MgCl₂, 10 μM pargyline, 1 mM ascorbate, 1.2 mM NaH₂PO₄ and 25 mM NaHCO₃, adjusted to pH 7.4). The slices were then washed with 0.9% NaCl and incubated in physiological medium with 0.1 μM [³H]norepineprine (30 minutes, 37° C.). The slices were again washed with 0.9% NaCl and then placed in tubes (borosilicate glass, 12×75 mm) containing 0.5 ml Mg⁺²-free physiological medium with corticosterone and desipramine added to minimize norepinephrine reuptake. Samples were analyzed for [³H] content at 5 minute intervals. After 75 minutes, the inhibitor drug was added. Fifteen minutes later, NMDA was added to a concentration of 150 μM. The amount of [³H] released was measured by liquid scintillation spectroscopy. The amount of NMDA-induced [³H] release in the presence of the inhibitor was compared to the amount of NMDA-induced [³H] release in the absence of the inhibitor to obtain comparative data for percent inhibition calculations.

Thus, the compounds of this invention demonstrate the ability to antagonize NMDA-induced lethality in vivo in mice (Table 1). They did not compete with 3-(2-carboxypiperazinyl-4-yl)-propyl-1-phosphonic acid (CPP), a known competitive NMDA-antagonist, for its binding site in rat frontal cortex homogenates. Compounds of the present invention antagonize NMDA-induced norepinephrine release from rat hippocampal slices. The compounds of the present invention are, therefore, noncompetitive NMDA antagonists.

Compounds of the present invention showed efficacy ratios for antagonizing NMDA-induced lethality over ataxia superior to those seen with PCP, MK-801, dextromethorphan and dextrorphan (Table 1). In addition, they were more potent than dextromethorphan and dextrorphan in antagonizing NMDA-induced lethality.

Compounds of the present invention are orally active against NMDA-induced lethality. This combination or oral activity, greater potency with respect to dextromethorphan and dextrorphan, and better efficacy ratios relative to standard NMDA antagonists, including PCP, MK-801, dextromethorphan, and dextrorphan, makes the compounds of this invention superior to presently available noncompetitive NMDA antagonists. Compounds with such a profile are useful in the treatment of CNS disorders such as senile dementia, Alzheimer's disease, Huntingdon's chorea, stroke, hypoglycemia, cerebral palsy, cerebral ischemia, epilepsy, and olivo-ponto cerebellar atrophy.

Hence, there is herewith provided in addition to the novel compounds, supra, a method for preventing neurodegenerative disorders induced by overstimulation of excitatory amino acid receptors in brain and spinal cord, which comprises administering to a mammal suffering from such degenerative disease states, an NMDA antagonist of the formula:

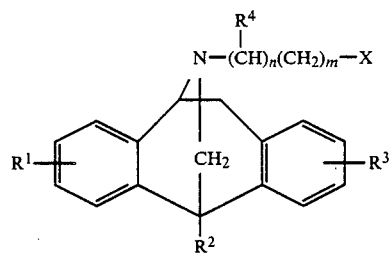

in which $R^1$ and $R^3$ are, independently, hydrogen, alkyl of 1 to 6 carbon atoms, alkoxy of 1 to 6 carbon atoms, hydroxy, cyano, nitro, halo, trifluoromethyl, amino, alkylamino of 1 to 6 carbon atoms or dialkylamino of 2 to 12 carbon atoms;

$R_2$ is alkyl of 1 to 6 carbon atoms;

$R^4$ is alkyl of 1 to 6 carbon atoms, phenyl or benzyl;

n is 0 or 1;

m is one of the integers 0, 1, 2, 3, 4, 5 or 6; and

X is alkyl of 1 to 6 carbon atoms, alkylamino of 1 to 6 carbon atoms, dialkylamino in which each alkyl group has 1 to 6 carbon atoms, alkanoyl of 2 to 6 carbon atoms or substituted or unsubstituted phenyl, pyridinyl, pyrimidinyl, pyrazinyl, quinolyl, morpholinyl, furyl, thienyl, pyrrolyl, tetrahydrofuryl, tetrahydrothienyl, pyrrolidinyl, piperidinyl, piperazinyl or perhydropyrimidinyl, in which the substituents is alkyl of 1 to 6 carbon atoms, alkoxy of 1 to 6 carbon atoms, halo, trifluoromethyl, cyano, nitro or hydroxy;

or a pharmaceutically acceptable salt thereof.

As such, the compounds of this invention may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compounds can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

To determine the effective amount of compound to be administered in alleviation of CNS degenerative dysfunctions, the physician need only evaluate the effects of a given NMDA antagonist in the patient by incrementally increasing the oral dosage from about 1 mg/kg to about 20 mg/kg until the desired symptomatic relief level is achieved. The continuing dose regimen may then be modified to achieve the desired result, with the range of about 1 to 100 mg/day. Similar techniques are followed by determining the effective dose range upon i.v. or i.m. administration. When using the compounds prophylactically to arrest declining cognitive function as in Alzheimer's dementia, a more subjective approach is taken such as by relating the drug dosage to improved memory responses or analogous desired responses which can be related to relief of overstimulation of the excitatory amino acid receptors.

What is claimed is:

1. A compound of the formula:

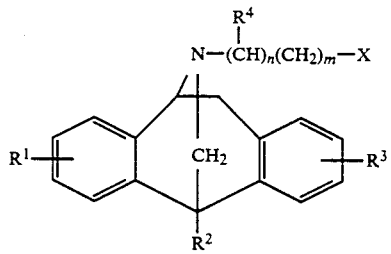

in which $R^1$ and $R^3$ are, independently, hydrogen, alkyl of 1 to 6 carbon atoms, alkoxy of 1 to 6 carbon atoms, hydroxy, cyano, nitro, halo, trifluoromethyl, amino, alkylamino of 1 to 6 carbon atoms or dialkylamino of 2 to 12 carbon atoms;

$R_2$ is alkyl of 1 to 6 carbon atoms;

$R^4$ is alkyl of 1 to 6 carbon atoms, phenyl or benzyl;

n is 0 or 1;

m is one of the integers 0, 1, 2, 3, 4, 5 or 6; and

X is alkyl of 1 to 6 carbon atoms, alkylamino of 1 to 6 carbon atoms, dialkylamino in which each alkyl group has 1 to 6 carbon atoms, alkanoyl of 2 to 6 carbon atoms or substituted or unsubstituted phenyl, pyridinyl, pyrimidinyl, pyrazinyl, quinolyl, morpholinyl, furyl, thienyl, pyrrolyl, tetrahydrofuryl, tetrahydrothienyl, pyrrolidinyl, piperidinyl, piperazinyl or perhydropyrimidinyl, in which the substituent is alkyl of 1 to 6 carbon atoms, alkoxy of 1 to 6 carbon atoms, halo, trifluoromethyl, cyano, nitro, or hydroxy;

or a pharmaceutically acceptable salt thereof.

2. A compound of claim 1 of the formula:

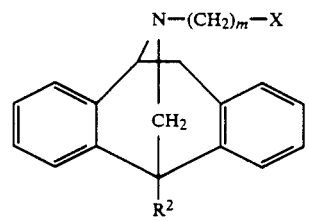

in which $R^2$ is alkyl of 1 to 3 carbon atoms;

m is one of the integers 0, 1, 2, 3 or 4; and

X is alkyl of 1 to 4 carbon atoms, alkylamino of 1 to 4 carbon atoms, dialkylamino of 2 to 8 carbon atoms, alkanoyl of 2 to 4 carbon atoms, phenyl, pyridinyl, 2-pyrimidinyl, 2-pyrazinyl, 2-quinolinyl, 2-furyl, 2-thienyl or 2-pyrrolyl;

or a pharmaceutically acceptable salt thereof.

3. A compound of claim 1 which is 10,11-dihydro-5,12-dimethyl-10,5-(iminomethano)-5H-dibenzo[a,d]cycloheptene, or a pharmaceutically acceptable salt thereof.

4. A compound of claim 1 which is 10,11-dihydro-5-methyl-12-[2-(2-pyridinyl)ethyl]10,5-(iminomethano-5H-dibenzo[a,d]cycloheptene, or a pharmaceutically acceptable salt thereof.

5. A compound of claim 1 which is 10,11-dihydro-5-methyl-12-[2-(4-pyridinyl)ethyl]10,5-(iminomethano)-5H-dibenzo[a,d]cycloheptene, or a pharmaceutically acceptable salt thereof.

6. A compound of claim 1 which is 10,11-dihydro-5-methyl-12-(2-pyrazinylethyl)-10,5-(iminomethano)-5H-dibenzo-cycloheptene, or a pharmaceutically acceptable salt thereof.

7. A compound of claim 1 which is 10,11-dihydro-N,N,5-trimethyl-10,5-(iminomethano)-5H-dibenzo[a,d]cycloheptene-12-propanamine, or a pharmaceutically acceptable salt thereof.

8. A compound of claim 1 which is 10,11-dihydro-5-methyl-12-(2-pyridinyl-methyl)-10,5-(iminomethano)-5H-dibenzo[a,d]cycloheptene, or a pharmaceutically acceptable salt thereof.

9. A compound of claim 1 which is 10,11-dihydro-5-methyl-12-[2-(2-quinolinyl)ethyl]-10,5-(iminomethano)-5H-dibenzo[a,d]cycloheptene, or a pharmaceutically acceptable salt thereof.

10. A compound of claim 1 which is 10,11-dihydro-5-methyl-12-[2-(6-methyl-2-pyridinyl)ethyl]-10,5-(iminomethano)-5H-dibenzo[a,d]cycloheptene, or a pharmaceutically acceptable salt thereof.

11. A compound of claim 1 which is 10,11-dihydro-5-methyl-12-(2-phenylethyl)-10,5-(iminomethano)-5H- dibenzo[a,d]cycloheptene, or a pharmaceutically acceptable salt thereof.

12. A compound of claim 1 which is 10,11-dihydro-5-methyl-12-(2-propyl)-10,5-(iminomethano)-5H-dibenzo[a,d]cycloheptene, or a pharmaceutically acceptable salt thereof.

13. A compound of claim 1 which is 10,11-dihydro-5-methyl-10,5-(iminomethano)-5H-dibenzo[a,d]cycloheptene-12-acetamide, or a pharmaceutically acceptable salt thereof.

* * * * *